US010058544B2

(12) United States Patent
Bahl et al.

(10) Patent No.: US 10,058,544 B2
(45) Date of Patent: Aug. 28, 2018

(54) (S)-N-(3-(6-ISOPROPOXYPYRIDIN-3-YL)-1H-INDAZOL-5-YL)-1-(2-(4-(4-(1-METHYL-1H-1,2,4-TRIAZOL-3-YL)PHENYL)-3,6-DIHYDROPYRIDIN-1(2H)-YL)-2-OXOETHYL)-3-(METHYLTHIO) PYRROLIDINE-3-CARBOXAMIDE COMPOSITIONS FOR PHARMACEUTICAL PREPARATIONS

(71) Applicant: Merck Sharp & Dohme Corp., Rahway, NJ (US)

(72) Inventors: Deepak Bahl, Princeton, NJ (US); Yung-Chi Lee, New Providence, NJ (US); Alfred Lee, Robbinsville, NJ (US); William Anthony Marinaro, Jr., Scotch Plains, NJ (US); Dan Zhang, Watchung, NJ (US); Tao Feng, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/536,467

(22) PCT Filed: Dec. 14, 2015

(86) PCT No.: PCT/US2015/065434
§ 371 (c)(1),
(2) Date: Jun. 15, 2017

(87) PCT Pub. No.: WO2016/100152
PCT Pub. Date: Jun. 23, 2016

(65) Prior Publication Data

US 2018/0000803 A1 Jan. 4, 2018

Related U.S. Application Data

(60) Provisional application No. 62/094,515, filed on Dec. 19, 2014.

(51) Int. Cl.
*A61K 31/416* (2006.01)
*C07D 403/04* (2006.01)
*A61K 31/435* (2006.01)
*A61K 31/444* (2006.01)
*A61K 9/16* (2006.01)

(52) U.S. Cl.
CPC .......... *A61K 31/444* (2013.01); *A61K 9/1623* (2013.01); *A61K 9/1652* (2013.01); *A61K 2300/00* (2013.01)

(58) Field of Classification Search
CPC .............. A61K 2300/00; A61K 31/444; A61K 9/1623; A61K 9/1652
See application file for complete search history.

(56) References Cited

U.S. PATENT DOCUMENTS

2010/0310651 A1 12/2010 Mittal
2011/0065746 A1 3/2011 Sugihara et al.
2011/0183973 A1 7/2011 Baldwin et al.
2014/0309234 A1 10/2014 Oehlen et al.

FOREIGN PATENT DOCUMENTS

WO 2009105500 A1 8/2009

*Primary Examiner* — Alma Pipic
(74) *Attorney, Agent, or Firm* — Richard S. Parr; Catherine D. Fitch

(57) ABSTRACT

The invention includes a granular composition comprising the active ingredient (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, wherein a total amount of active ingredient comprises by weight % about 60-90% (S)—N-(3-(6-isopro-poxypyridin-3-yl)-1H-indazol-5-yl)-1-(2-(4-(4-(1-methyl-1H-1,2,4-triazol-3-yl)phenyl)-3,6-di-hydropyridin-1(2H)-yl)-2-oxoethyl)-3-(methylthio)pyrrolidine-3-carboxamide Form 1 HCl, about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio) pyrrolidine-3-carboxamide amorphous free base.

5 Claims, 4 Drawing Sheets

(S)-N-(3-(6-ISOPROPOXYPYRIDIN-3-YL)-1H-INDAZOL-5-YL)-1-(2-(4-(4-(1-METHYL-1H-1,2,4-TRIAZOL-3-YL)PHENYL)-3,6-DIHYDROPYRIDIN-1(2H)-YL)-2-OXOETHYL)-3-(METHYLTHIO) PYRROLIDINE-3-CARBOXAMIDE COMPOSITIONS FOR PHARMACEUTICAL PREPARATIONS

This application is a National Stage application of PCT/US2015/065434, filed Dec. 14, 2015, which claims the benefit of U.S. Provisional Application Ser. No. 62/094,515, filed Dec. 19, 2014, all of which is incorporated herein by reference in its entirety.

BACKGROUND OF THE INVENTION

WO2009/105500 describes ERK inhibitors, including procedures for making them and procedures for preparing pharmaceutical compositions comprising the ERK inhibitors. Described pharmaceutical compositions include solid form preparations including powders, tablets, dispersible granules, capsules, cachets and suppositories for direct administration to a patient; liquid form preparations including solutions, suspensions and emulsions for direct administration to a patient; aerosol preparations suitable for inhalation; solid form preparations which are intended to be converted, shortly before use, to liquid form preparations, including solutions, suspensions and emulsions for subsequent administration to a patient; and transdermal compositions including creams, lotions, aerosols and/or emulsions for direct application to the patient or administration via transdermal patch.

(S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, a specific ERK inhibitor described in WO2009/105500, can exist in several crystalline forms as well as an amorphous form. During formulation processing, certain forms, such as (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline Form 1 HCl, can become converted into other forms. Depending on process conditions, roller compaction of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline Form 1 HCl can result in creation of significant amounts of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base, and mechanical stress can result in creation of significant amounts of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl. In order to efficiently prepare safe and effective oral (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline Form 1 HCl pharmaceutical tablet and capsules compositions for administration to patients, it is highly desirable to create (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide granules that minimize conversion from the crystalline Form 1 HCl to the amorphous free base and amorphous HCl salt form.

The present invention provides granules of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline Form 1 HCl which are used for efficient preparation of tablets and capsules comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline Form 1 HCl that is suitable for safe and effective oral administration to a patient.

SUMMARY OF THE INVENTION

The invention includes a granular composition comprising the active ingredient (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, wherein a total amount of active ingredient comprises by weight % about 60-90% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl (also referred to as HCl Form 1), about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

DETAILED DESCRIPTION OF THE INVENTION

Figure 1:
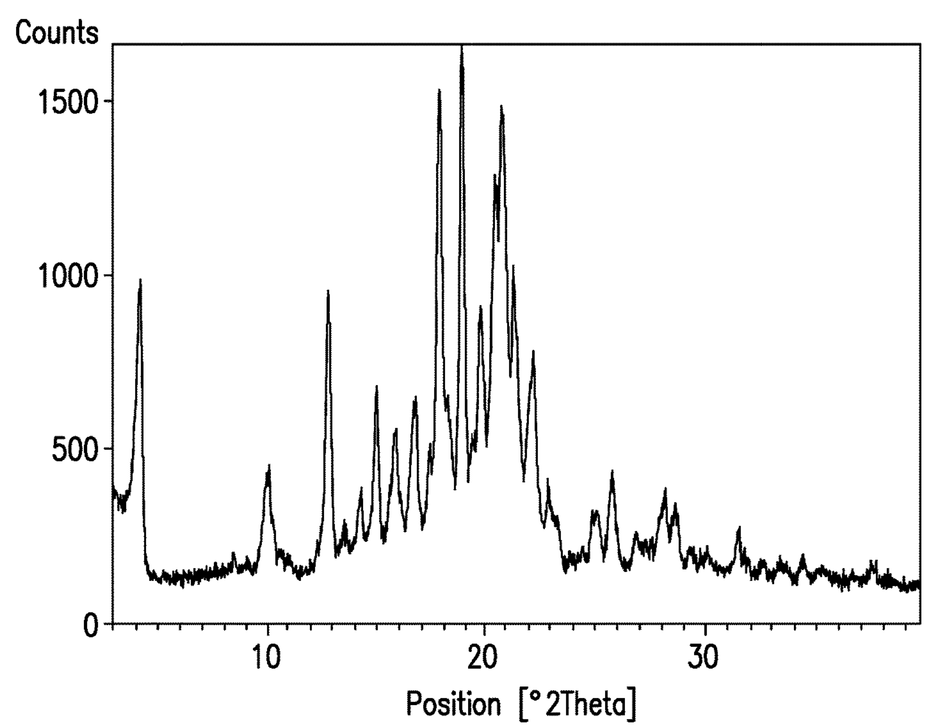
FIG. 1 shows the powder x-ray diffraction pattern for free base hydrate (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 2.

The invention is a pharmaceutical tablet comprising the active ingredient (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, wherein a total amount of active ingredient comprises by weight % about 60-90% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base in one embodiment of the invention, the total amount of active ingredient comprises by weight % about 70-85% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-25% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

The invention is also a granular composition comprising the active ingredient (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, wherein a total amount of active ingredient comprises by weight % about 60-90% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base. In an embodiment of the invention, the total amount of active ingredient comprises by weight % about 70-85% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-25% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

The invention is also a process for preparing a granular composition of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl which comprises the steps of:

a) dry mixing lactose, microcrystalline cellulose, (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl and a disintegrant in a high shear granulator to form a dry mix, b) adding a binder solution comprising water and polyvinyl pyrrolidone to the high shear granulator to form a wet granulation of the dry mix formed in step a), c) drying the wet granulation with dry heat to form dry granules wherein a total amount of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide in the granules comprises by weight % about 60-90% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

The invention is also a process for preparing a granular composition of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl which comprises the steps of:

a) dry mixing lactose, microcrystalline cellulose, polyvinyl pyrrolidone, (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl and a disintegrant in a high shear granulator to form a dry mix, b) adding a binder solution comprising water to the high shear granulator to form a wet granulation of the dry mix formed in step a), c) drying the wet granulation with dry heat to form a dry granules wherein a total amount of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide in the granules comprises by weight % about 60-90% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

The invention is also a process for preparing a granular composition of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl which comprises the steps of:

a) dry mixing lactose, microcrystalline cellulose, (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl and a disintegrant in a high shear granulator to form a dry mix, b) heating the dry mix with fluid air until the mix temperature is 55°-60° C., c) maintaining the mix temperature and adding a binder solution comprising water and polyvinyl pyrrolidone to the high shear granulator to form wet granules of the dry mix formed in step a), d) drying the wet granules with fluid air to form dry granules, wherein a total amount of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide in the granules comprises by weight % about 60-90% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

The invention is also a process for preparing a granular composition of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl which comprises the steps of:

a) dry mixing lactose, microcrystalline cellulose, polyvinyl pyrrolidone, (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl and a disintegrant in a high shear granulator to form a dry mix, b) heating the dry mix with fluid air until the mix temperature is 55°-60° C., c) maintaining the mix temperature and adding a binder solution comprising water to the high shear granulator to form wet granules of the dry mix formed in step a), d) drying the wet granules with fluid air to form dry granules, wherein a total amount of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide in the granules comprises by weight % about 60-90% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

(S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, structure I below:

I

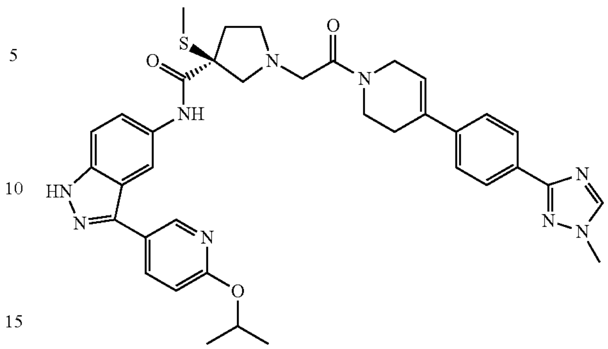

and methods for its preparation, is described in patent publication WO2009/105500 (compound A6). (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide is also available from Active Biochem CAT #A-1191. The compound, which inhibits ERK activity (i.e., ERK1 and ERK2 activity), may be useful for treating a broad spectrum of cancers, such as, for example, melanoma, pancreatic cancer, thryroid cancer, colorectal cancer, lung cancer, breast cancer, and ovarian cancer.

Preparation:

(S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide free base synthesis is a 19 step process. Compound preparation is divided into three intermediate preparations A, B and C followed by coupling of the intermediates. All intermediates start with commercially available compounds. Compound 5 is prepared by reaction of the commercially available bromo-4-cyanobenzene with methyl hydrazine under acidic conditions to form the hydrazinoimidate 2 in modest yield. After reaction with formic acid in two steps the bromophenyl-N-methyl triazole intermediate 3 is obtained. The tetrahydropyridine ring is introduced by a Suzuki reaction of the commercially available Boc protected tetrahydropyridine-boronate to obtain the tricyclic ring system 4. Chloroacetamide 5 is obtained in excellent yield by reaction of the deprotected 4 with chloroacetylchloride. The pyrrolidine core 10a is obtained in good yield in 5 steps starting from commercially available 6. Reaction with thionylchloride gave the thiomethyl olefin 7. Cycloaddition (2+3) gives 8 followed by removal of the benzyl protection group to give 9. L-Tartaric acid resolution of the pyrrolidine core gives the pure (S) enantiomer 9 after filtration from methanol. After protection as the Boc derivative and hydrolysis of the methyl ester, 10 is obtained in overall 50% yield. Compound 17 is obtained from commercially available indazole 11. Bromination at the 3-position of indazole 11 proceeds in excellent yield without chromatography to obtain 12. Suzuki reaction of the bromo compound 12 with 14 gives the nitro indazole 16 after chromatography. Reduction of 16 gives aniline 17 as an oil in quantitative yield without chromatography. The final coupling of the intermediates proceeded by coupling 17 with 10a to obtain 18 in good yield. After deprotection of the Boc and Trityl groups the final coupling with 5 gave (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3- carboxamide after chromatography. Final purification is carried out by crystallization from methanol/diethylether. This synthetic route has been conducted on a scale that delivered (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide free base (Compound I).

Synthesis from Key Intermediates 5, 10 and 17

Preparation A:

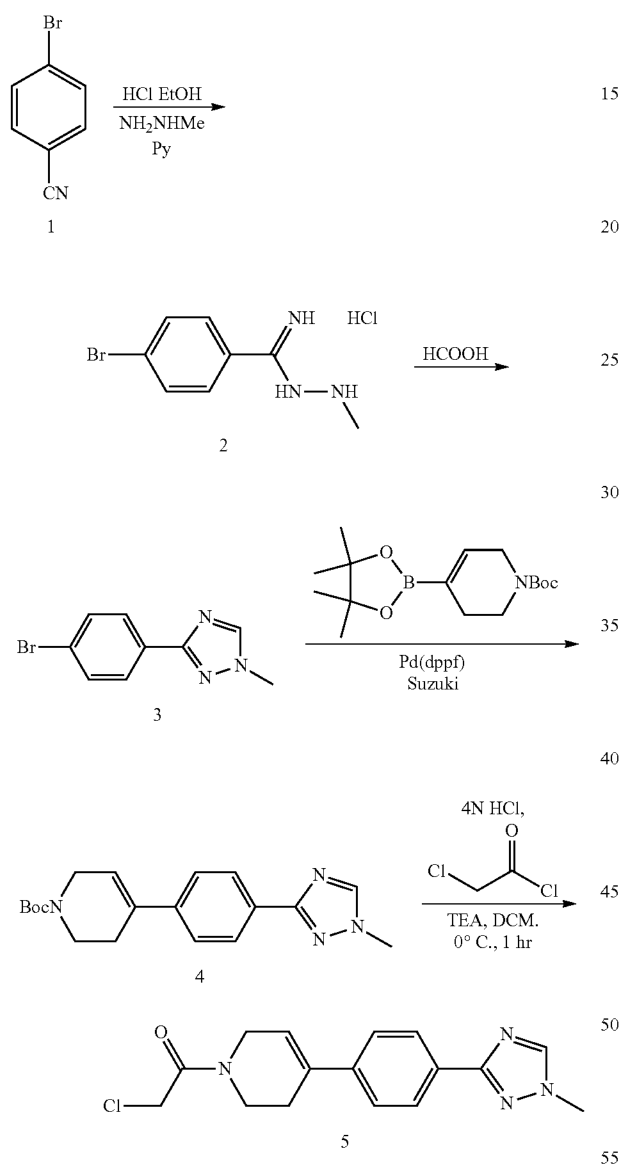

Preparation B:

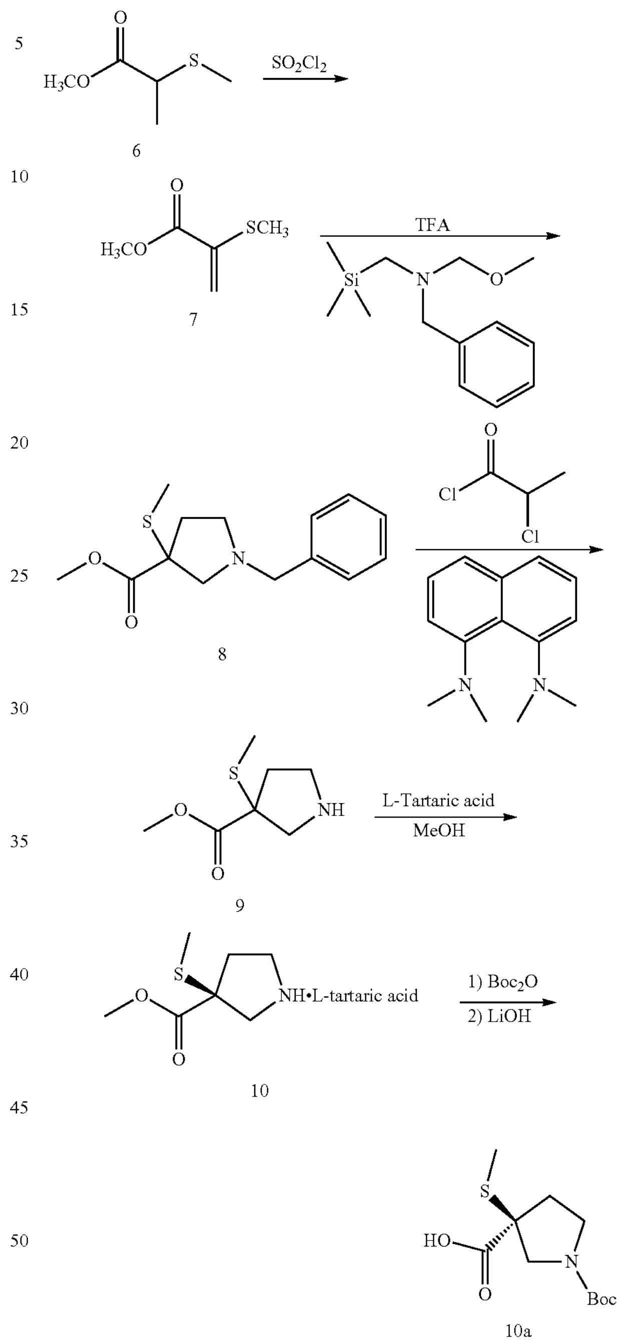

Preparation C:

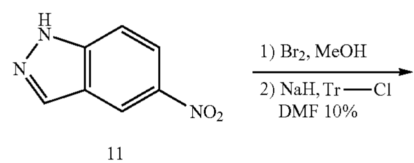

-continued
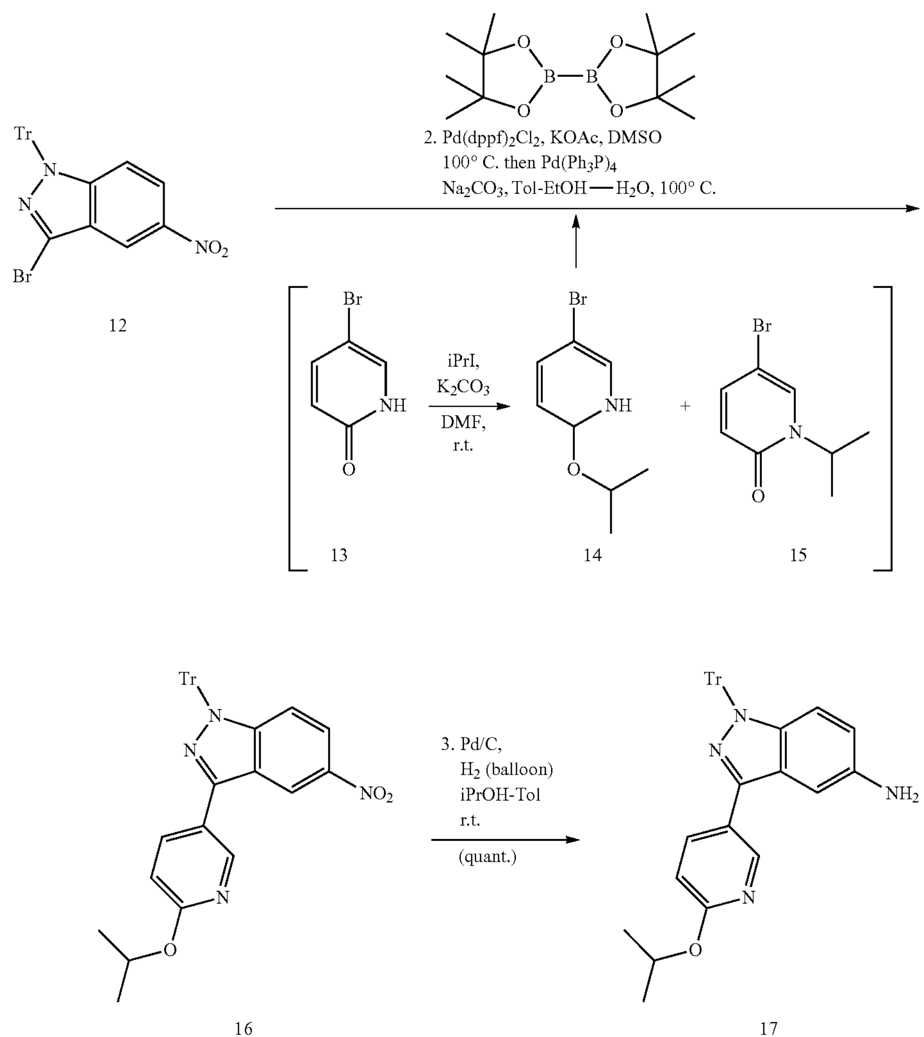
Final Coupling:
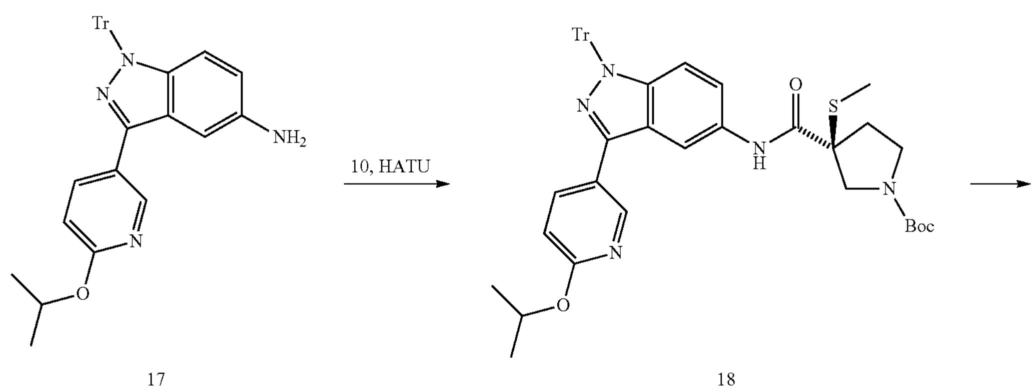

-continued

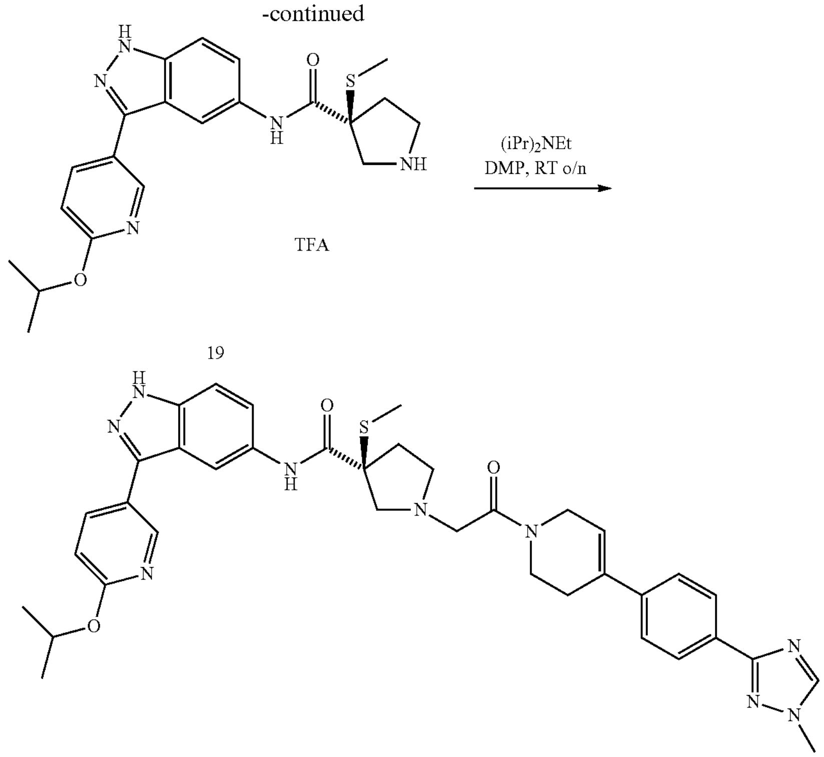

Compound I

Preparation of Free Base Hydrate Form 2

Compound I was suspended in neat water at ambient temperature. Mixture was aged for at least one day yielding a crystalline form (Free Base Hydrate Form 2).

Preparation of HCl Form 1

HCl Hydrate Form 1 or HCl Hydrate Form 2 was suspended in ethyl acetate, toluene, acetonitrile, isopropyl acetate, acetone or tetrahydrofuran (THF) at ambient temperature. Mixtures were aged for at least one day yielding a crystalline form (HCl Form 1).

Preparation of HCl Hydrate Form 1

Compound I was suspended in aqueous isopropanol mixtures followed by the addition of hydrochloric acid. Mixtures were aged at ambient temperature for at least one day yielding a crystalline salt (HCl Hydrate Form 1).

Preparation of HCl Hydrate Form 2

Compound I was suspended in aqueous acetone mixtures followed by the addition of hydrochloric acid. Mixtures were aged at ambient temperature for at least one day yielding a crystalline salt (HCl Hydrate Form 2).

HCl Form 1 was suspended in neat water at ambient temperature. Mixture was aged for at least one day yielding a crystalline form (HCl Hydrate Form 2).

Free Base Hydrate Form 2 Powder X-Ray Diffraction Data (FIG. 1)

| 2-Θ, ° | d-spacing, Å | Relative Intensity, % |
|---|---|---|
| 4.24 | 20.82 | 44 |
| 10.04 | 8.81 | 19 |
| 12.78 | 6.92 | 49 |
| 13.48 | 6.57 | 7 |
| 14.22 | 6.23 | 14 |
| 14.98 | 5.91 | 30 |
| 15.79 | 5.61 | 26 |
| 16.76 | 5.29 | 29 |
| 17.92 | 4.95 | 82 |
| 18.89 | 4.70 | 100 |
| 19.70 | 4.51 | 49 |
| 20.41 | 4.35 | 74 |
| 20.76 | 4.28 | 87 |
| 21.26 | 4.18 | 56 |
| 22.16 | 4.01 | 40 |
| 22.85 | 3.89 | 16 |
| 24.88 | 3.58 | 11 |
| 25.75 | 3.46 | 18 |
| 26.85 | 3.32 | 8 |
| 28.16 | 3.17 | 14 |
| 28.67 | 3.11 | 13 |
| 29.37 | 3.04 | 5 |
| 31.52 | 2.84 | 8 |
| 33.60 | 2.67 | 2 |
| 34.50 | 2.60 | 3 |
| 37.72 | 2.39 | 3 |

Figure 2:
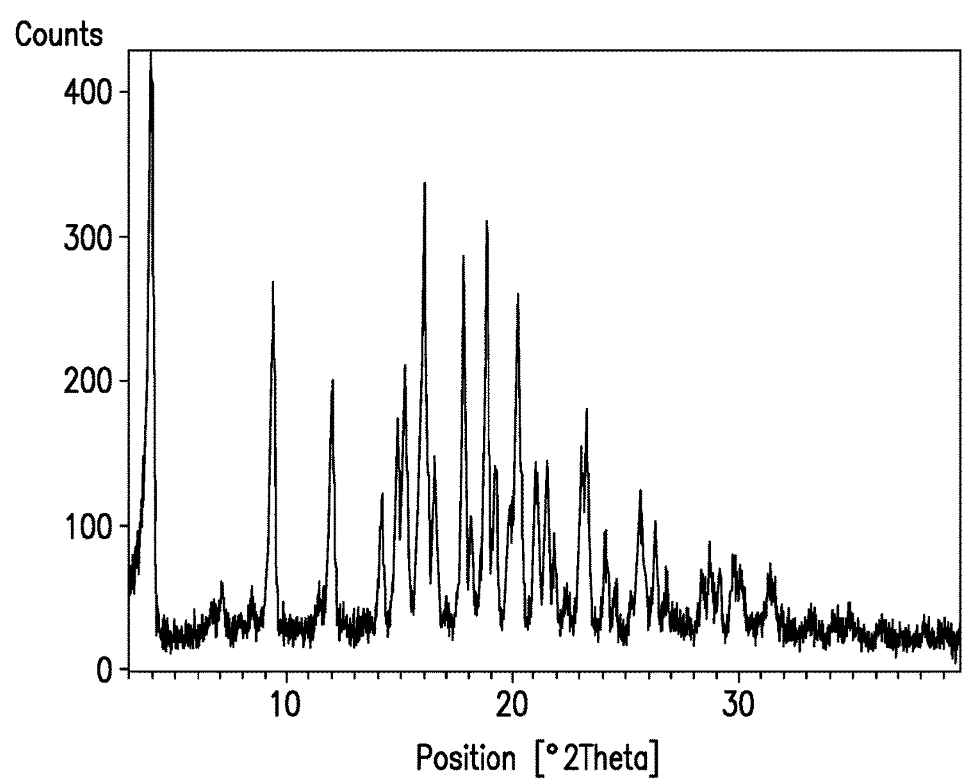
FIG. 2 shows the powder x-ray diffraction pattern for HCl (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1.

HCl Form 1 Powder X-Ray Diffraction Data (FIG. 2)

| 2-Θ, ° | d-spacing, Å | Relative Intensity, % |
|---|---|---|
| 3.99 | 22.14 | 100 |
| 7.08 | 12.49 | 8 |

-continued

| 2-Θ, ° | d-spacing, Å | Relative Intensity, % |
|---|---|---|
| 8.44 | 10.48 | 6 |
| 9.39 | 9.42 | 53 |
| 11.95 | 7.41 | 46 |
| 14.14 | 6.26 | 24 |
| 14.80 | 5.99 | 37 |
| 15.17 | 5.84 | 46 |
| 16.00 | 5.54 | 71 |
| 16.51 | 5.37 | 32 |
| 17.78 | 4.99 | 67 |
| 18.12 | 4.90 | 20 |
| 18.81 | 4.72 | 75 |
| 19.22 | 4.62 | 31 |
| 20.20 | 4.40 | 61 |
| 21.02 | 4.23 | 29 |
| 21.55 | 4.12 | 30 |
| 21.85 | 4.07 | 17 |
| 22.37 | 3.97 | 8 |
| 23.05 | 3.86 | 32 |
| 23.31 | 3.82 | 34 |
| 24.12 | 3.69 | 16 |
| 25.59 | 3.48 | 21 |
| 26.34 | 3.38 | 18 |
| 26.85 | 3.32 | 12 |
| 28.73 | 3.11 | 15 |
| 29.17 | 3.06 | 12 |
| 29.81 | 3.00 | 13 |
| 30.17 | 2.96 | 11 |
| 31.35 | 2.85 | 10 |
| 33.21 | 2.70 | 4 |
| 34.84 | 2.58 | 3 |
| 36.42 | 2.47 | 2 |

Figure 3:
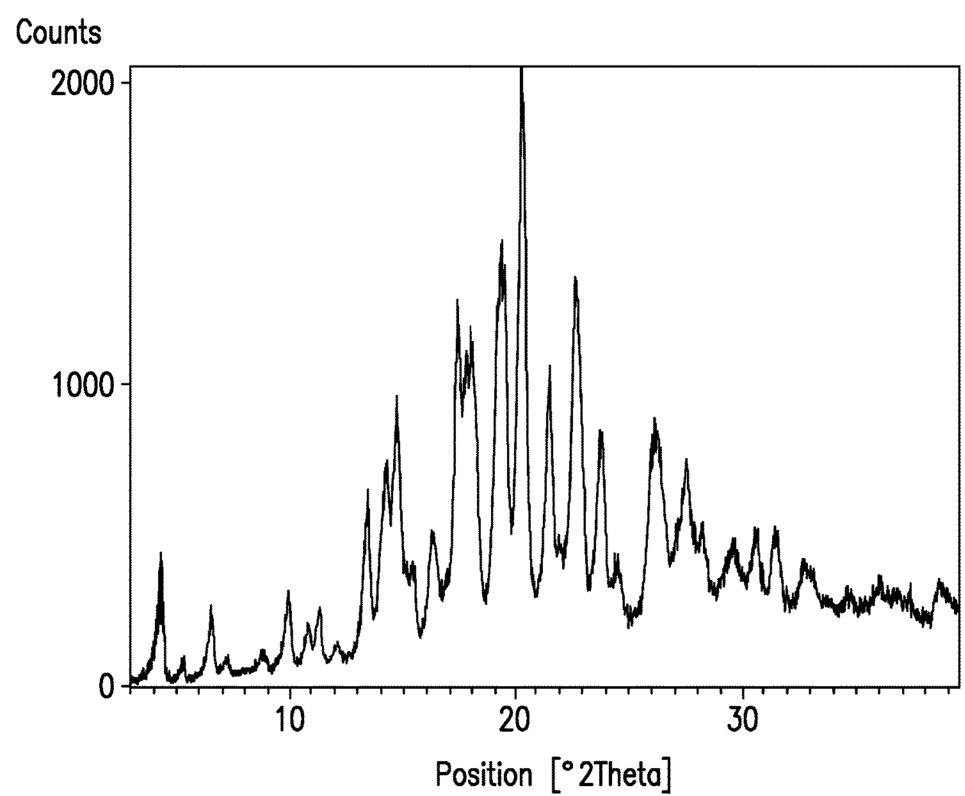
FIG. 3 shows the powder x-ray diffraction pattern for HCl hydrate (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1.

HCl Hydrate Form 1 Powder X-Ray Diffraction Data (FIG. 3)

| 2-Θ, ° | d-spacing, Å | Relative Intensity, % |
|---|---|---|
| 4.34 | 20.38 | 16 |
| 5.31 | 16.63 | 2 |
| 6.57 | 13.45 | 9 |
| 7.20 | 12.28 | 3 |
| 8.79 | 10.07 | 3 |
| 9.93 | 8.91 | 11 |
| 10.76 | 8.22 | 7 |
| 11.25 | 7.87 | 9 |
| 12.03 | 7.36 | 3 |
| 13.39 | 6.61 | 25 |
| 14.12 | 6.27 | 32 |
| 14.67 | 6.04 | 41 |
| 15.38 | 5.76 | 14 |
| 16.22 | 5.46 | 21 |
| 17.31 | 5.12 | 59 |
| 18.17 | 4.88 | 43 |
| 19.08 | 4.65 | 54 |
| 19.41 | 4.57 | 67 |
| 20.21 | 4.39 | 100 |
| 21.42 | 4.15 | 45 |
| 22.58 | 3.94 | 63 |
| 23.77 | 3.74 | 33 |
| 24.50 | 3.63 | 12 |
| 26.11 | 3.41 | 35 |
| 27.51 | 3.24 | 28 |
| 28.25 | 3.16 | 15 |
| 29.57 | 3.02 | 13 |
| 30.61 | 2.92 | 14 |
| 31.47 | 2.84 | 14 |
| 32.70 | 2.74 | 7 |
| 38.69 | 2.33 | 5 |

Figure 4:
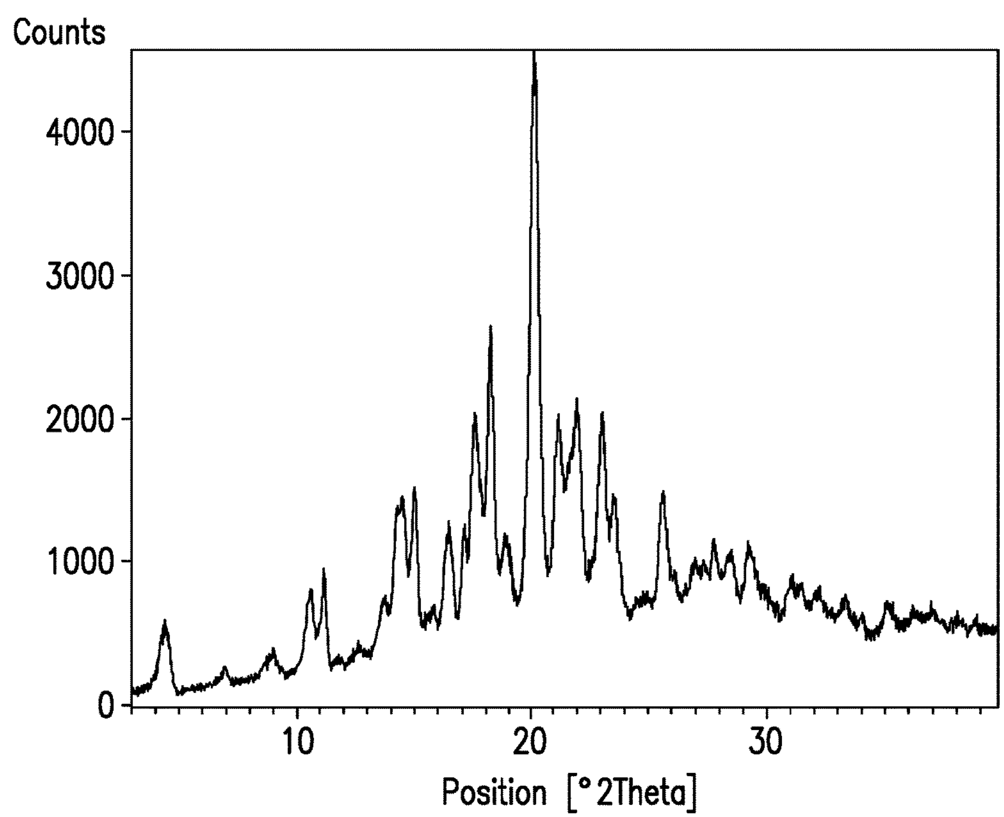
FIG. 4 shows the powder x-ray diffraction pattern for HCl hydrate (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 2.

HCl Hydrate Form 2 Powder X-Ray Diffraction Data (FIG. 4)

| 2-Θ, ° | d-spacing, Å | Relative Intensity, % |
|---|---|---|
| 4.53 | 19.49 | 15 |
| 7.07 | 12.51 | 3 |
| 9.10 | 9.72 | 5 |
| 10.69 | 8.27 | 15 |
| 11.24 | 7.87 | 18 |
| 13.76 | 6.44 | 12 |
| 14.29 | 6.20 | 27 |
| 14.58 | 6.08 | 28 |
| 15.03 | 5.90 | 30 |
| 16.60 | 5.34 | 22 |
| 17.16 | 5.17 | 23 |
| 17.59 | 5.04 | 42 |
| 18.31 | 4.85 | 58 |
| 18.95 | 4.68 | 21 |
| 20.20 | 4.40 | 100 |
| 21.17 | 4.20 | 41 |
| 22.01 | 4.04 | 42 |
| 23.05 | 3.86 | 41 |
| 23.57 | 3.78 | 27 |
| 25.65 | 3.47 | 27 |
| 26.99 | 3.30 | 14 |
| 27.81 | 3.21 | 18 |
| 28.53 | 3.13 | 15 |
| 29.24 | 3.05 | 16 |
| 31.07 | 2.88 | 9 |
| 32.25 | 2.78 | 8 |
| 33.44 | 2.68 | 6 |
| 35.26 | 2.55 | 4 |
| 36.85 | 2.44 | 2 |

Granulation

In the pharmaceutical industry, granulation refers to the act or process in which primary powder particles are made to adhere to form larger, multiparticle entities called granules. It is the process of collecting particles together by creating bonds between them. Bonds are formed by compression or by using a binding agent. Granulation is extensively used in the manufacturing of tablets and pellets (or spheroids).

Granulation is carried out for various reasons, one of those is to prevent the segregation of the constituents of powder mix. Segregation is due to differences in the size or density of the component of the mix. Normally, the smaller and/or denser particles tend to concentrate at the base of the container with the larger and/or less dense ones on the top. An ideal granulation will contain all the constituents of the mix in the correct proportion in each granule and segregation of granules will not occur.

The granulation process combines one or more powder particles and forms a granule that will allow tableting or spheronization processes to be within required limits. This way a predictable and repeatable process is possible and quality tablets or pellets can be produced using tabletting or spheronization equipment. Many powders, because of their small size, irregular shape or surface characteristics, are cohesive and do not flow well. Granules produced from such a cohesive system will be larger and more isodiametric, both factors contributing to improved flow properties.

Some powders are difficult to compact even if a readily compactable adhesive is included in the mix, but granules of the same powders are often more easily compacted. This is associated with the distribution of the adhesive within the granule and is a function of the method employed to produce the granule.

For example, if one were to make tablets from granulated sugar versus powdered sugar, powdered sugar would be difficult to compress into a tablet and granulated sugar would be easy to compress. Powdered sugar's small particles have poor flow and compression characteristics. These small particles would have to be compressed very slowly for a long period of time to make a worthwhile tablet. Unless the powdered sugar is granulated, it could not efficiently be made into a tablet that has good tablet characteristics such as uniform content or consistent hardness.

In wet granulation, granules are formed by the addition of a granulation liquid onto a powder bed which is under the influence of an impeller (in a High shear granulator, screws (in a twin screw granulator) or air (in a fluidized bed granulator)). The agitation resulting in the system along with the wetting of the components within the formulation results in the aggregation of the primary powder particles to produce wet granules. The granulation liquid (fluid) contains a solvent which must be volatile so that it can be removed by drying, and be non-toxic. Typical liquids include water, ethanol and isopropanol either alone or in combination. The liquid solution can be either aqueous based or solvent based. Aqueous solutions have the advantage of being safer to deal with than solvents. The fluidized bed system provides a bed of solid particles with a stream of air or gas passing upward through the particles at a rate great enough to set them in motion. As the air travels through the particle bed, it imparts unique properties to the bed.

For example, the bed behaves as a liquid. It is possible to propagate wave motion, which creates the potential for improved mixing. In a bubbling fluidized bed, no temperature gradient exists within the mass of the fluidized particles. This isothermal property results from the intense particle activity in the system. Thus, the fluid bed can be used to dry the wet product, agglomerate particles, improve flow properties, instantize the product, or produce coated particles for controlled release or taste masking. Modular systems designed to carry out multiple processes in which only a container change is necessary to change the type of unit operation being performed have been developed by all the manufacturers of fluid bed processors.

Water mixed into the powders can form bonds between powder particles that are strong enough to lock them together. However, once the water dries, the powders may fall apart. Therefore, water may not be strong enough to create and hold a bond. In such instances, a liquid solution that includes a binder (pharmaceutical glue) is required. Povidone, which is a polyvinyl pyrrolidone (PVP), is one of the most commonly used pharmaceutical binders. PVP is dissolved in water or solvent and added to the process. When PVP and a solvent/water are mixed with powders, PVP forms a bond with the powders during the process, and the solvent/water evaporates (dries). Once the solvent/water has been dried and the powders have formed a more densely held mass, then the granulation is milled. This process results in the formation of granules.

The process can be very simple or very complex depending on the characteristics of the powders, the final objective of tablet making, and the equipment that is available. In the traditional wet granulation method the wet mass is forced through a sieve to produce wet granules which are subsequently dried.

Dry granulation is sometimes used to form granules without using a liquid solution because the product granulated may be sensitive to moisture and heat. Forming granules without moisture requires compacting and densifying the powders. In this process the primary powder particles are aggregated under high pressure. Sweying granulator or high shear mixer-granulator can be used for the dry granulation.

Dry granulation can be conducted under two processes; either a large tablet is produced in a heavy duty tableting press or the powder is squeezed between two counter-rotating rollers to produce a continuous sheet or ribbon of materials (roller compactor, commonly referred to as a chilsonator).

When a tablet press is used for dry granulation, powders may not possess enough natural flow to feed the product uniformly into the die cavity, resulting in varying degrees of densification. The roller compactor (granulator-compactor) uses an auger-feed system to deliver powder between two pressure rollers. Powders are compacted between the rollers into a ribbon or small pellets and milled through a low-shear mill. The products are passed through a mill and final blend before tablet compression.

Tablets comprising granules of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide prepared via high shear wet granulation can be formed using conventional tableting procedures and vehicles and other excipients including diluents (such as lactose, avicel, mannitol, dibasic calcium phosphate) disintegrants (such as croscarmellose sodium, crospovidone, sodium starch glycollate), salt disintegrants (such as NaCl, $NaHCO_3$, $KH_2PO_4$, $K_2SO_4$, KCl), binders (such as povidone, hydroxypropyl methylcellulose, hydroxypropyl cellulose), glidants/flow promoters (such as silicon di-oxide), and lubricants (magnesium stearate, sodium stearyl fumarate) to improve the chemical stability of the formulation.

Tablet Prepared Using Roller Compaction (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline form 1 HCl was subjected to roller compaction in order to create a granular composition for subsequent use in preparing tablets of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline form 1 HCl.

Three tablets (RC-1, RC-2 and RC-3) having the following amounts (weight %) of ingredients were prepared using roller compaction.

| | RC-1 | RC-2 | RC-3 |
|---|---|---|---|
| Intragranular | | | |
| F-1 HCl | 26.3 | 26.3 | 26.3 |
| Lactose Monohydrate | 33 | 33 | 33 |
| Microcrystalline cellulose | 30.7 | 30.7 | 30.7 |
| Croscarmellose sodium | 5.0 | — | 5.0 |
| Crospovidone | — | 5.0 | — |
| Silicon dioxide | 2.0 | 2.0 | 2.0 |
| Magnesium stearate | 2.0 | 2.0 | — |
| Sodium stearyl fumarate | — | — | 2.0 |
| Extragranular | | | |
| Magnesium stearate | 1.0 | 1.0 | — |
| Sodium stearyl fumarate | — | — | 1.0 |
| Total | 100 | 100 | 100 |

"F-1 HCl" is (S)—N-(3-(6-isopropoxypyridin-3-yl)-1H-indazol-5-yl)-1-(2-(4-(4-(1-methyl-1H-1,2,4-triazol-3-yl) phenyl)-3,6-dihydropyridin-1(2H)-yl)-2-oxoethyl)-3-(methylthio)pyrrolidine-3-carboxamide crystalline form 1 HCl.

The following procedure was followed:

1. Blend colloidal silicon dioxide and (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline form 1 HCl in a blender.
2. Delump the blend using a screen.
3. Blend lactose monohydrate, microcrystalline cellulose (Avicel 102), and disintegrant (croscarmellose sodium or crospovidone) with the delumped materials from step 2 using a blender.
4. Add prescreened magnesium stearate lubricant to the blend of step 3 and blend.
5. Roller compact the blend resulting from step 4
6. Screen the roller compacted ribbons through a mesh and add the resulting milled granules to a suitable bin.
7. Add prescreened extragranular magnesium stearate lubricant to the bin and blend with the milled granules.
8. Compress the final lubricated blend resulting from step 7 using a suitable rotary tablet press.

Tablets prepared via roller compaction resulted in creation of significant amounts of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl and (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base, including amounts of the free base of greater than 5%. "LOD" refers to "limit of detection" and "<LOD" means the amount of indicated material, if any, was not detectable.

| | F-1 HCl | Am HCl | Am FB | F-1 FB |
|---|---|---|---|---|
| Starting material | 92 | 7 | <LOD | <LOD |
| RC-1 | 72 | 18 | 9 | <LOD |
| RC-1 | 78 | 17 | 5 | <LOD |
| RC-1 | 72 | 20 | 8 | <LOD |
| RC-2 | 67 | 16 | 17 | <LOD |
| RC-3 | 67 | 16 | 17 | <LOD |

"F-1 HCl" is (S)—N-(3-(6-isopropoxypyridin-3-yl)-1H-indazol-5-yl)-1-(2-(4-(4-(1-methyl-1H-1,2,4-triazol-3-yl) phenyl)-3,6-dihydropyridin-1(2H)-yl)-2-oxoethyl)-3-(methylthio)pyrrolidine-3-carboxamide crystalline form 1 HCl. "Am HCl" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl. "Am FB" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base. "F-1 FB" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio) pyrrolidine-3-carboxamide crystalline form 1 free base.

Example 1

Tablet Prepared Using Wet Granulation

Wet granulation of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline form 1 HCl was achieved using a high shear granulator. High shear wet granulation was alternatively achieved using a fluidized bed procedure. Wet granulation processing resulted in no disproportionation of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline form 1 HCl.

Two tablets (1a and 1b) having the following amounts (weight %) of ingredients were prepared using wet granulation.

| | 1a | 1b |
|---|---|---|
| Intragranular | | |
| F-1 HCl | 52.7 | 52.7 |
| Lactose Monohydrate | 16.3 | 16.3 |
| microcrystalline cellulose | 20.0 | 20.0 |
| Croscarmellose sodium | 4.0 | — |
| Crospovidone | — | 4.0 |
| Polyvinylpyrrolidone K30 | 5.0 | 5.0 |
| Extragranular | | |
| Croscarmellose sodium | 1.0 | — |
| Crospovidone | — | 1.0 |
| Magnesium stearate | 1.0 | 1.0 |
| Total | 100 | 100 |

High Shear Wet Granulation:

The following procedure was followed:

1. Prepare a 20% binder solution by adding purified water and polyvinyl pyrrolidone K30 to a mixing vessel and stir until completely dissolved.
2. Add lactose, microcrystalline cellulose (Avicel 102), (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline form 1 HCl and a disintegrant (croscarmellose sodium or crospovidone) to a high shear granulator.
3. Dry mix the ingredients using an impeller and chopper.
4. Add the binder solution prepared in step 1 to the high shear granulator using a peristaltic pump and flexible tubing.
5. Spray the binder solution to form wet granules. Additional mixing without spraying of the binder solution (also known as wet massing) may be used.
6. Pass the wet granulation through a screen.
7. Dry the granules using a tray dryer and dry heat.
8. Pass the dried granules through a screen and add to a bin.
9. Add extragranular disintegrant (croscarmellose sodium or crospovidone) to the materials in step 8 and blend.
10. Add prescreened magnesium stearate lubricant to the bin and blend.
11. Compress the lubricated blend resulting from step 10 using a suitable rotary tablet press.

Fluidized Bed Granulation:

1. Prepare a 20% binder solution by adding purified water and PVP K30 to a mixing vessel and stir until completely dissolved.
2. Add lactose monohydrate, microcrystalline cellulose, (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-

(methylthio)pyrrolidine-3-carboxamide crystalline form 1 HCl and croscarmellose sodium or crospovidone disintegrant to a fluid bed to form a mixture.
3. Pre-heat the materials of step 2 using fluid air until the target bed temperature reaches 55°-60° C.
4. Spray the binder solution prepared in step 1 onto the mixture resulting from step 2 to form wet granules.
5. Fluidize and dry the wet granules resulting from step 4.
6. Pass the dried granules through a screen and add to a bin
7. Add extragranular croscarmellose sodium or crospovidone disintegrant to the dried granules and blend.
8. Add prescreened magnesium stearate lubricant to the blend resulting from step 7 and blend.
9. Compress the final lubricated blend using a suitable rotary tablet press.

In contrast to roller compaction process, wet granulation of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline form 1 HCl generated only two physical species. The absence of disproportionation of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide HCl salt is completely unexpected and non-obvious as presence of moisture should induce more disproportionation of the (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide HCl salt. In fact one would intuitively assume that there will be more disproportionation via wet granulation and would not pursue this option.

Tablets prepared via wet granulation resulted in creation of some (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, but no detectable amounts of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base, and no detectable amounts of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline form 1 free base. "LOD" refers to "limit of detection" and "<LOD" means the amount of indicated material, if any, was not detectable.

| | F-1 HCl | Am HCl | Am FB | F-1 FB |
|---|---|---|---|---|
| Starting material | 92 | 7 | LOD | LOD |
| 1a | 74 | 26 | LOD | LOD |
| 1b | 75 | 25 | LOD | LOD |
| 1b | 74 | 23 | LOD | LOD |
| 1b | 71 | 26 | LOD | LOD |

"F-1 HCl" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline form 1 HCl. "Am HCl" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl. "Am FB" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base. "F-1 FB" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline form 1 free base.

What is claimed is:

1. A pharmaceutical tablet comprising the active ingredient (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, wherein a total amount of active ingredient comprises by weight % about 60-90% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

2. A pharmaceutical tablet of claim 1 wherein the total amount of active ingredient comprises by weight % about 70-85% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-25% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

3. A granular composition comprising the active ingredient (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, wherein a total amount of active ingredient comprises by weight % about 60-90% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

4. A granular composition of claim 3 wherein the total amount of active ingredient comprises by weight % about 70-85% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-25% (S)—N-(3-(6-isopropoxypyridin-3-yl)-1H-indazol-5-yl)-1-(2-(4-(4-(1-methyl-1H-1,2,4-triazol-3-yl)phenyl)-3,6- dihydropyridin-1(2H)-yl)-2-oxoethyl)-3-(methylthio) pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

5. A process for preparing a granular composition of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl which comprises the steps of:

a) dry mixing lactose, microcrystalline cellulose, polyvinyl pyrrolidone, (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl and a disintegrant in a high shear granulator to form a dry mix, b) adding a binder solution comprising water to the high shear granulator to form a wet granulation of the dry mix formed in step a), c) drying the wet granulation with dry heat to form a dry granules wherein a total amount of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide in the granules comprises by weight % about 60-90% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Form 1 HCl, about 10-30% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous HCl, and about 0-5% (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous free base.

* * * * *